(12) United States Patent
Jordan

(10) Patent No.: US 8,231,623 B1
(45) Date of Patent: Jul. 31, 2012

(54) BONE REDUCTION AND PLATE CLAMP ASSEMBLY

(76) Inventor: Christopher Jordan, Midwest City, OK (US)

( * ) Notice: Subject to any disclaimer, the term of this patent is extended or adjusted under 35 U.S.C. 154(b) by 207 days.

(21) Appl. No.: 12/806,172

(22) Filed: Aug. 6, 2010

Related U.S. Application Data

(60) Provisional application No. 61/281,846, filed on Nov. 23, 2009.

(51) Int. Cl.
*A61B 17/00* (2006.01)
*A61F 4/00* (2006.01)
*A61F 5/04* (2006.01)

(52) U.S. Cl. .......... 606/54; 606/86 R; 606/250; 606/251

(58) Field of Classification Search .................. 606/54, 606/57–60, 250–253, 260, 278, 282, 90, 606/105, 86 R
See application file for complete search history.

(56) References Cited

U.S. PATENT DOCUMENTS

| | | | |
|---|---|---|---|
| 2,362,957 A | 11/1944 | Hackett | |
| 2,427,128 A | 9/1947 | Ettinger | |
| 3,477,429 A | 11/1969 | Sampson | |
| 4,187,840 A | 2/1980 | Watanabe | |
| 5,563,349 A | 10/1996 | Burke | |
| 5,797,919 A | 8/1998 | Brinson | |
| 6,605,088 B1 | 8/2003 | St. Onge | |
| 6,623,483 B1 * | 9/2003 | Kazakov et al. | ................ 606/57 |
| 6,921,404 B2 | 7/2005 | Bimman | |
| 2008/0009871 A1 | 1/2008 | Orbay | |
| 2009/0177234 A1 * | 7/2009 | Butler et al. | .................. 606/277 |

* cited by examiner

*Primary Examiner* — Eduardo C Robert
*Assistant Examiner* — Christina Negrelli
(74) *Attorney, Agent, or Firm* — Randal D. Homburg

(57) ABSTRACT

A pair of clamps are attached to a damaged bone one each side of a fracture site during a surgical reduction, one clamp on each side of the fracture site, after which the two clamps are slidably engaged to a single pivotal alignment bar, with the clamps then being adjusted to properly align the bone for a surgical attachment using a bone plate which is secured between the respective bone and each respective clamp, holding the bone in place with the bone in proper alignment for the attachment of screws through the plate into the bone, stabilizing the fracture site during the plate attachment procedure.

5 Claims, 6 Drawing Sheets

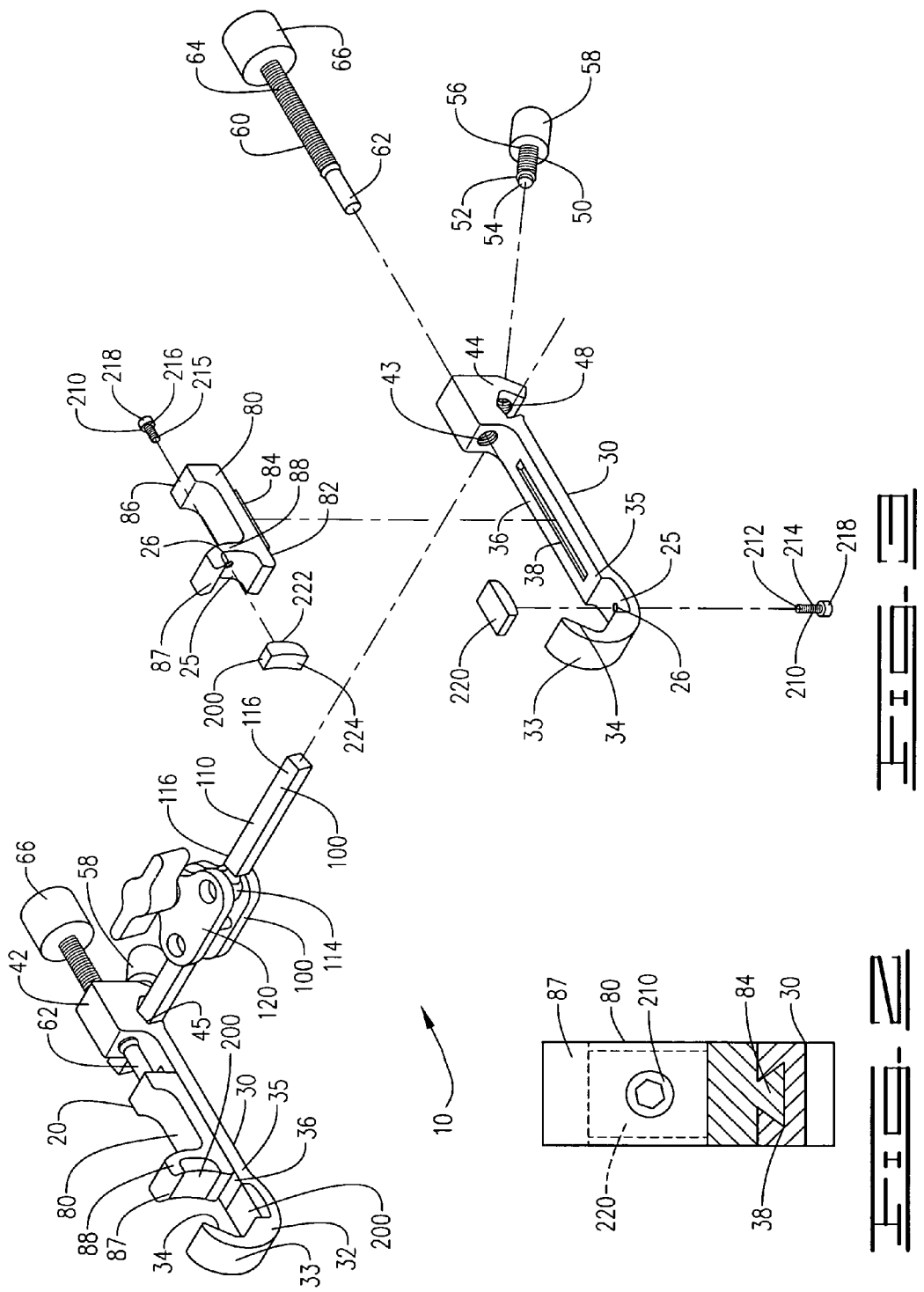

BONE REDUCTION AND PLATE CLAMP ASSEMBLY

CROSS REFERENCE TO RELATED APPLICATIONS

This Application claims the benefit of Provisional Patent Application No. 61/281,846 filed on Nov. 23, 2009, by the same inventor, Christopher Jordan.

I. BACKGROUND OF INVENTION

1. Field of the Invention

A pair of clamps are attached to a damaged bone one each side of a fracture site during a surgical reduction, one clamp on each side of the fracture site, after which the two clamps are slidably engaged to a single pivotal alignment bar, with the clamps then being adjusted to properly align the bone for a surgical attachment using a bone plate which is secured between the respective bone and each respective clamp, holding the bone in place with the bone in proper alignment for the attachment of screws through the plate into the bone, stabilizing the fracture site during the plate attachment procedure.

2. Description of Prior Art

A preliminary review of prior art patents was conducted by the applicant which reveal prior art patents in a similar field or having similar use. However, the prior art inventions do not disclose the same or similar elements as the present bone reduction and plate clamp assembly, nor do they present the material components in a manner contemplated or anticipated in the prior art. Those patent include the following patent within the relevant field of art.

Prior art has demonstrated several linear alignment clamps which have been used in surgical applications for bone reduction. In U.S. Pat. No. 4,187,840 to Watanabe, a linear bone clamp is disclosed having a base member with a guideway and an abutment face on a sliding member. However the base member fails to disclose attachment to any alignment bar. There is an attachment to a handle, but the handle is undefined within the disclosed prior art. It also lacks any secondary means to position a bone plate between the clamp and the bone once the bone is secured. A linear bone clamp is also disclosed in U.S. Pat. No. 2,362,957 to Hackett, but is has no V-shaped clamping face nor does it attach to any alignment bar. Its stated purpose is to hold bone fragments in place during a surgical procedure and its disclosed function is as a singular clamping instrument. U.S. Pat. No. 3,477,429 demonstrates a linear clamp with a detachable clamping portion which is installed upon a bone and then the handle portion is withdrawn, leaving only the locked clamping members in place. It is used upon the fracture site to hold the fracture site in place permanently secured about the fracture site.

A diametral extensometer is disclosed in U.S. Pat. No. 5,563,349 which appears to be a type of clamp meant to hold a cylindrical shaft within three circumferential points around the cylinder using three individually extended plates mounted within a semicircular frame, with each extended plate being independently extended towards a central point to hold the shaft about its circumference with radial adjustment, using a plurality of V-shaped contact surfaces.

The only surgical clamping tool which indicates the use of a pair of clamps with an alignment bar is U.S. Pat. No. 6,605,088 to St. Onge. In that patent, a pair of bone clamps further attach to an alignment bar. The clamp indicates several element of similar nature, but a subjective reading of the patent shows distinct difference between the claimed components of the present clamping assembly and that of St. Onge.

The alignment bar is strictly linear, and is demonstrated and claimed as being telescopic. This linear adjustment does not provide for a pivotally adjusted assembly nor does it disclose at least one pivotal means of allowing for the alignment bar to provide anything but a two-dimensional alignment of the bar and the clamps. It is noted that the clamps may be rotated upon the bar at several angles, but the bar itself is not pivotal. The bar is also rounded and does not indicate a square profile or a secure connection to each alignment bar to provide the clamps in a manner to fully immobilize and a stable reduction of the bone during application of a plate during the surgical procedure. It also does not conform the connection to the clamp within a square bar receiving notch with a screw forced against a squared edge to maximize the force between the screw and the alignment bar for this secure attachment between the clamp and the alignment bar. St. Onge further fails to disclose the secondary clamp adjustment means to secure the clamp to a bone and then further secure a bone plate between the clamp and the bone.

II. SUMMARY OF THE INVENTION

During a surgical reduction of a displaced fracture of a bone, human or other animal, the bone must be aligned and stabilized for the application of a surgical plate using surgical screws to secure the bone fracture together to allow it to heal in proper alignment. A surgeon must manually manipulate the bone section into a proper alignment and then either hold the bones together to apply the plate in place or use the hands of several other assistants to perform the maneuvers required during the surgical repair process.

The present set of clamps and a single alignment bar provide the clamps to be clamps to the fractured bone on each side of the fracture, attaching the clamps to the alignment bar and sliding the clamps along the bar to align and adjust the bone to reduce the fracture site to its utmost contact alignment. A surgical plate may then be inserted between the bone and the clamps surfaces and resecured to hold the plate against the bone surfaces where the surgeon deems most appropriate, with the plate then being secured using screws or other bone plate securing means without the plate being misplaced and without the bone being misaligned during the surgical reduction and repair.

III. DESCRIPTION OF THE DRAWINGS

The following drawings are informal drawings submitted with this provisional patent application.

FIG. 2 is a sectional view along reference lines 2/2 of FIG. 1.

FIG. 3 is an exploded view of one linear bone clamp and one embodiment of the pivotal alignment bar attached to an assembled linear bone clamp.

FIG. 6 is a sectional view of a linear bone clamp along section lines 6/6 of FIG. 4.

IV. DESCRIPTION OF THE PREFERRED EMBODIMENT

Figure 1:
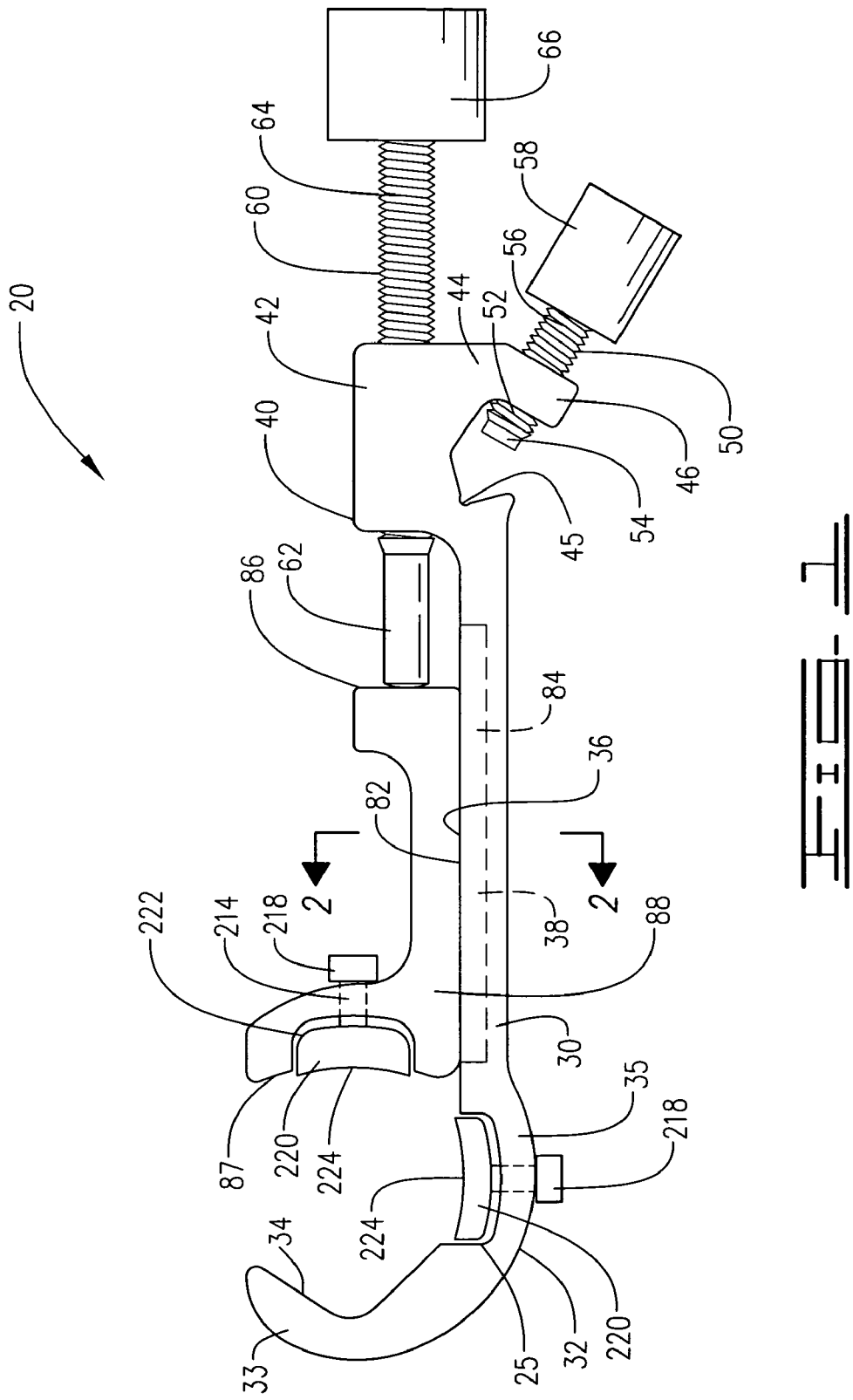
FIG. 1 is a side view of a linear bone clamp with the retractable clamp arm in a retracted position.

A linear bone clamp assembly 10, shown in FIGS. 1-7B of the drawings, comprises a pair of linear bone clamps 20 and a pivotal alignment bar 100, each linear bone clamp 20 attaching to a fractured bone A during a surgical repair of the bone, one on each side of the fracture site B, with each clamp 20 being further attached to the pivotal alignment bar 100 to reduce the fracture site and properly align the bone, with a bone plate C being inserted between each clamp 20 and its respective bone location, to secure the plate C to the bone A to stabilize the bone fracture site B for complete healing.

Each linear bone clamp 20, FIGS. 1-6, provides a base clamp member 30 having a first end 32 defining a first clamp plate 33 having an inner V-shaped clamping margin 34, a neck portion 35 providing an upper margin 36 defining a linear channel 38, and a second end 40 defining a base 42 having a central linear inner threaded bore 43 and an upper extension 44 defining a transverse bar receiving notch 45 and an angled bar collar 46 having an inner threaded bore 48 directed into the bar receiving notch 45, an angled outer threaded set screw 50 threaded through the angled inner threaded bore 48 with a first end 52 defining a bar engaging tip 54 directed towards the bar receiving notch 45 and a second end 56 having an extended cylindrical head 58, a sliding clamp member 80 having a lower surface 82 defining an outward linear channel extension 84 slideably engaging the linear channel 38 of the base clamp member 30, a first end 86 defining a sliding clamp face 87 and a second end 88 rotatably attaching to a first end 62 of an outer threaded clamping screw 60, the outer threaded clamping screw 60 threadably engaging the central linear inner threaded bore 43 of the base clamp member 30 and having a second end 64 having an extended cylindrical head 66 for rotating the outer threaded clamping screw 60, moving the sliding clamp member 80 along the linear channel 38 and moving the sliding clamp face 87 towards and away from the inner V-shaped margin 34 of the base clamp member 30, clamping a bone A between the inner V-shaped margin and the V-shaped clamp face.

The bar receiving notch 45 is preferably presented with a square contour and that the pivotal alignment bar 100 includes at least two extending bar members 110 with a square profile, FIGS. 1 and 3-7B. The bar members 110 would be positioned within the bar receiving notch 45 with one presenting edge 118 directly aligning with the bar engaging tip 54 of the angled outer screw 50, FIG. 6, the bar engaging tip 54 secured against the presenting edge 118 of each bar member 110. The square profile bar members would be less likely to be subjected to slippage or rotational movement of the attached linear clamps 20 than would a rounded or cylindrical alignment bar, and the square contour of the bar receiving notch 45 of each linear clamp 20 would further prevent rotation of each alignment bar 110 even further.

FIG. 6 shows the linear clamp 20 in an closed position, with the V-shaped clamp face 34 and sliding clamp face 87 positioned against a bone A, shown in phantom lines. It is also contemplated that the V-shaped margin 34 and sliding clamp face 87 may be provided with texture or other friction enhancing aspects. The V-shape has been demonstrated in practice to significantly diminish the potential rotation or displacement of rounded or cylindrical objects grasped between it and an opposing clamping face over rounded or flat surfaces.

FIG. 2 indicates the sectional view of an embodiment of the sliding clamp member 80 and the base member 30 of each clamp indicating the relationship of a dove-tailed channel as the linear channel 38 on the base clamp member, and a dove tailed extension as the outward linear channel extension 84 extending from the lower surface 82 of the sliding clamp member 80. The connection, shown as a dove-tailed embodiment may, however, be provided as a slotted channel with a T-shaped extension tab which is slidably engaged with the slotted channel, not shown. It is not intended that the drawings figures are provided to limit the scope of the relationship between the sliding member 80 and the base member 30 slidable connections. The drawings merely indicate one working embodiment for illustration purposes.

Each linear clamp member 20 may also be provided with at least one secondary plate clamp 200 to allow for the secondary placement of a bone plate C between the bone A and each linear clamp member 20. Each secondary plate clamp 200 would require an axial recessed cavity 25 at the location within each linear clamp 20 where each secondary plate clamp 200 is located, as indicated in FIGS. 1, 3 and 6. As indicated in FIGS. 1, and 3-6, each secondary plate clamp 200 would further include a set screw 210 defining a first end 212 rotatably attached to a bone plate boot 220 on a rear surface 222, pushing or retracting a front surface 224 of each bone plate boot 220 from the axial recessed cavity 25 towards or away from a bone plate C positioned upon a bone A already secured within the linear bone clamp 20, the bone plate boot 220 moved by the rotation of the set screw 210. The set screw 210 further defines an outer thread 215 upon a shaft 214 which would engage a central threaded bore 26 within the axial recessed cavity 25 through the linear bone clamp 20 where the secondary clamp member 200 is placed, and an expanded head 218 which is formed on a second end 216 of the shaft 214 to manually rotate the set screw 210. In FIGS. 1 and 6, preferred locations include the secondary clamp member 200 located in the sliding clamp face 87 and also located between the clamp plate 33 and the neck portion 35 of the base clamp member 30, but these locations are merely illustrative and not intended to limit the location of the at least on secondary clamp member 200.

Figure 7A:
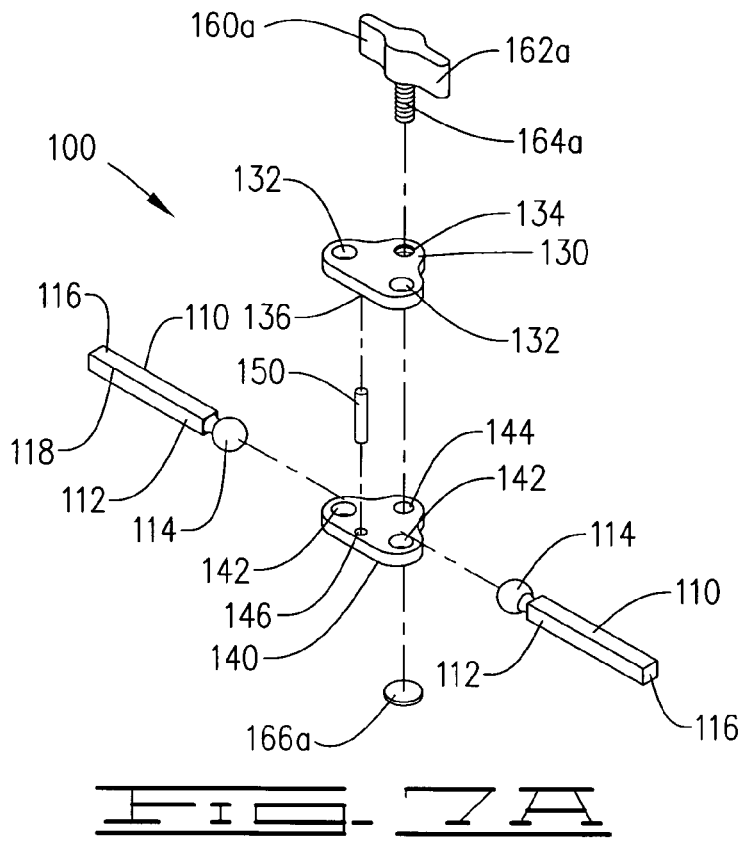
FIG. 7A is an exploded view of a first embodiment of the pivotal alignment bar.

The pivotal alignment bar 100 is provided with at least one pivotal locking member 120 and at least two extending bar members 110 having a square profile. Each bar member 110 further provides a rounded head 114 attached to a first end 112 of each bar member and a terminal end 116. Each rounded head 114 is attached within the pivotal locking member 120 and held in a static and locked position by a locking member screw 160a, 160b. A first embodiment of the pivotal locking member 120, FIGS. 3, 5 and 7A, provides the pivotal locking member with an upper triangular plate 130 having a two aligned circular apertures 132, a single offset internally threaded bore 134 and a locking pin hole 136 between the circular aligned apertures 132, a lower triangular plate 140 having two aligned circular apertures 142, an offset bore 144 and a locking pin hole 146 between the circular aligned apertures 142, a locking pin 150 connecting the locking pin holes 136, 146 together, and a locking screw 160a having an expanded head 162a and a threaded shaft 164a attached to a terminal end 166a through the offset bore 144 of the lower triangular plate 140 with the threaded shaft 164a contained within the offset internally threaded bore 134 of the upper triangular plate 130, wherein the each rounded head 114 of each bar member 110 is located within axially aligned circular apertures 132, 142 of the upper and lower triangular plates 130, 140 with the fixed locking pin 150 forcing the upper and lower triangular plates 130, 140 together, immovably placing the bar members 110 in a desired position for further connection to the paired linear bone clamps 20.

Figure 4:
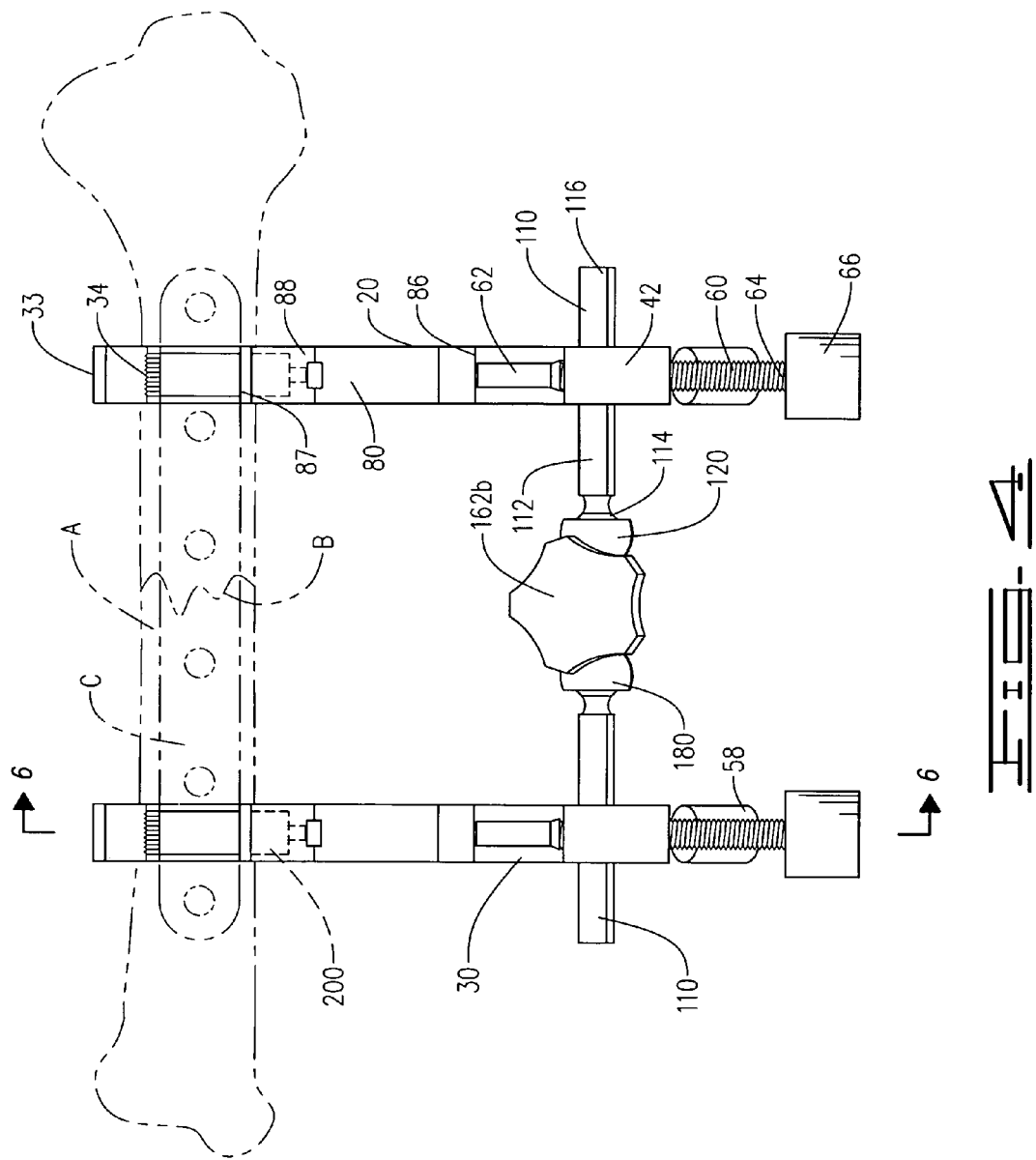
FIG. 4 is an upper view of the two clamps attached to a bone on each side of a fracture site, a linear bone in proper alignment and shown in phantom lines along with a phantom line bone plate, with the pivotal alignment bar positioned in a straight position.
Figure 7B:
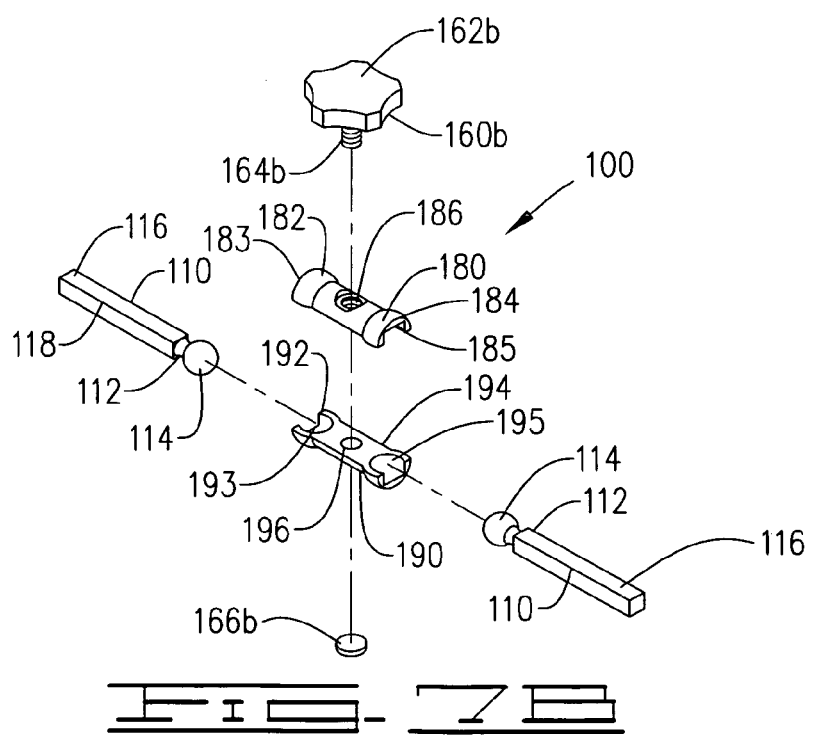
FIG. 7B is an exploded view of a second embodiment of the pivotal alignment bar.

A second embodiment of the pivotal locking member 120, shown in FIGS. 4 and 7B, provides the pivotal alignment bar 100 with the at least two extending bar members 110 having a square profile with a first end 112 having a rounded head 114 and a terminal end 116, and at least one pivotal locking member 120. This second embodiment pivotal locking member 120 defines an upper locking section 180 having a first rounded concave portion 183 on a first end 182 and a second rounded concave portion 185 on a second end 184, with a central internally threaded bore 186 between the first and second rounded concave portions 183, 185, a lower locking section 190 having a first rounded concave portion 193 on a first end 192 and a second rounded concave portion 195 on a second end 192, with a central bore 196 between the first and second rounded concave portions 193, 195, the upper and lower locking section 180, 190 being forced together with the concave portions 183, 193 and 185, 195, directed towards one another, capturing the rounded heads 114 of each respective bar member 110, by a locking screw 160b having an expanded head 162b and a threaded shaft 164b attached to a terminal end 166b rotatably attached through the central bore 196 of the lower locking section 190 with the threaded shaft 164b engaging the central internally threaded bore 186 of the upper locking section 180, forcing the upper and lower locking sections 180, 190 together immovably placing the bar members 110 in a desired position for further connection to the paired linear bone clamps 20.

It is contemplated that use of the assembly 10 would also involve a process or method, which would include steps of surgical site preparation, attachment of the bone clamps 20 to the respective bone segments in the appropriate locations, reduction of the bone, alignment of the bone clamps 20 securing the bone clamps to the pivotal alignment bar 100 and adjusting the alignment bar for stabilization of the bone in proper alignment and orientation, placement of the bone plate upon the bone across the fracture site, application of the bone plate to the bone fracture site and use of the secondary plate clamps 200 to secure the bone plate to the bone, removal of the clamps and post-surgical procedures following the bone reduction. The process may also be applied to the functional elements in the clamps and alignment bar prior to and including the period of time during the bone reduction and alignment procedure, the bone plate positioning and attachment, and the removal of the clamps subsequent to the surgical procedure.

Figure 5:
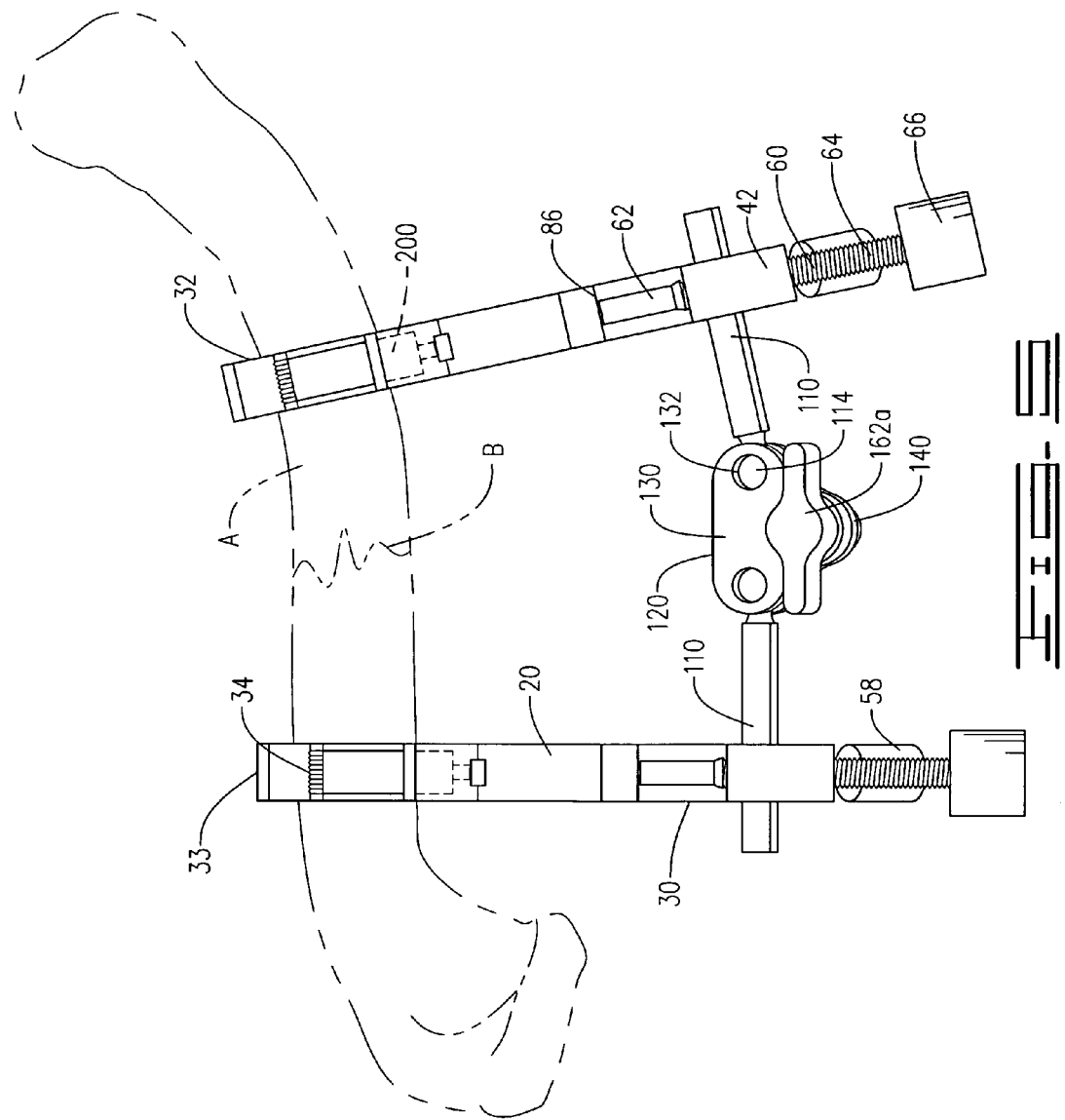
FIG. 5 is an upper view of the two clamps attached to a bone on each side of a fracture site, a curved bone in proper alignment and shown in phantom lines, with the pivotal alignment bar positioned at an angle.
Figure 8:
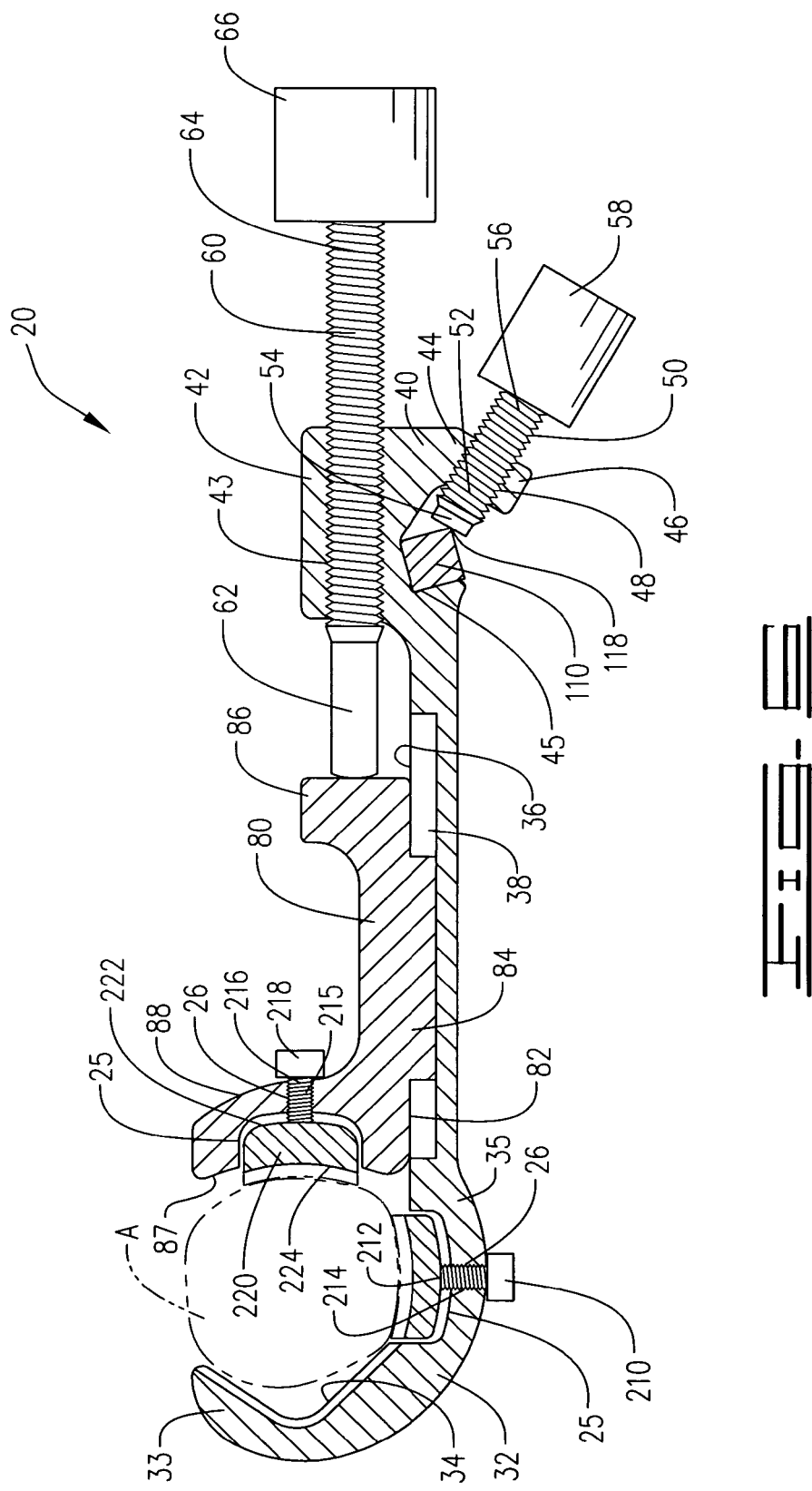

FIGS. 4 and 5 are the same general depiction of the bone clamps being used to stabilize the bone in proper alignment and prior to the installation of the bone plate to the bones at the fracture site. It is contemplated that other additional drawings may also be useful showing different aspects of the process for use of the clamps and alignment bar.

Although the embodiments of the bone clamps and alignment bar have been described and shown above, it will be appreciated by those skilled in the art that numerous modifications may be made therein without departing from the scope of the invention as herein described.

I claim:

1. A linear bone clamp assembly attaching to a fractured bone to reduce a fracture site and properly align the bone, also positioning a bone plate inserted between the linear bone clamp assembly and its respective bone location to secure the plate to the bone and complete the bone stabilization, the linear bone clamp assembly comprising:

at least two linear bone clamps, each linear bone clamp defining a base member with a first end defining a clamp face with a V-shaped clamping margin, a neck portion and an upper margin defining a linear channel, and a second end defining a base having a central inner threaded bore, an upper extension defining a square profiled receiving notch and an angled bar collar having an inner threaded bored within which is directed a first end of an angled outer threaded screw with said first end defining a bar engagement tip directed towards said receiving notch with a second end defining an expanded head to turn said angled outer screw, a sliding clamp member defining a lower surface having an outward linear channel extension which slideably secures within said linear channel of said base member, said sliding clamp member further defining a first end forming a sliding clamp face directed towards said clamp plate of said base member, and a second end secured to a first end of a clamping screw, said clamping screw threadably inserted through said central inner threaded bore of said base member and having a second end defining an expanded cylindrical head to turn said clamping screw, moving said sliding member towards and away from said clamp plate of said base member upon said upper margin of said base member, and at least one secondary plate clamp located upon said linear bone clamp within an axial recessed cavity within said linear bone clamp which may be extended from said linear bone clamp after said linear bone clamp is attached to a bone, to further secure a bone plate upon said bone for further attachment to said bone; and a pivotal alignment bar defining at least one locking member and at least two square profiled bar members extending from said at least one locking member.

2. The linear bone clamp assembly as disclosed in claim 1, said pivotal alignment bar further comprising:

said at least two extending bar members having a square profile, each said bar member further providing a rounded head attached to a first end of each said bar member and a terminal end, and said pivotal locking member defining an upper triangular plate having a two aligned circular apertures, a single offset internally threaded bore and a locking pin hole between said circular aligned apertures, a lower triangular plate having two aligned circular apertures, an offset bore and a locking pin hole between said circular aligned apertures, a locking pin connecting said locking pin holes together, and a locking screw having an expanded head and a threaded shaft attached to a terminal end through said offset bore of said lower triangular plate with said threaded shaft contained within said offset internally threaded bore of said upper triangular plate, wherein said each rounded head of each said bar member is located within said axially aligned circular apertures of said upper and lower triangular plates with said fixed locking pin forcing said upper and lower triangular plates together, immovably placing said bar members in a desired fixed position for further connection to said linear bone clamps.

3. The linear bone clamp assembly as disclosed in claim 1, said pivotal alignment bar further comprising:

at least two extending bar members having a square profile with a first end having a rounded head and a terminal end, and at least one pivotal locking member defining an upper locking section having a first rounded concave portion on a first end and a second rounded concave portion on a second end, with a central internally threaded bore between said first and second rounded concave portions, a lower locking section having a first rounded concave portion on a first end and a second rounded concave portion on a second end, with a central bore between said first and second rounded concave portions, said upper and lower locking section being forced together with said concave portions directed towards one another, capturing said rounded heads of each respective bar member, the force provided by a locking screw having an expanded head and a threaded shaft attached to a terminal end, rotatably attached through said central bore of said lower locking section with said threaded shaft engaging said central internally threaded bore of he upper locking section, forcing said upper and lower locking sections together immovably placing said bar members in a desired fixed position for further connection to said paired linear bone clamps.

4. The linear bone clamp assembly as disclosed in claim 1, said secondary plate clamp within said linear clamp further comprising:

an axial recessed cavity within each linear clamp wherein each secondary plate clamp is provided, and each said secondary plate clamp further defining a set screw having a first end rotatably attached to a bone plate boot on a rear surface, pushing or retracting a front surface of said bone plate boot from said axial recessed cavity towards or away from a bone plate positioned upon a bone already secured within said linear bone clamp, said bone plate boot moved by rotating said set screw, said set screw further defining an outer thread upon a shaft which would engage a central threaded bore within said axial recessed cavity through said linear bone clamp where said secondary clamp member is placed, and an expanded head formed on a second end of said shaft to provide fingertip manual rotation of said set screw.

5. The linear bone clamp assembly as disclosed in claim 1, said secondary plate clamp being located within said neck portion of said base member and within said sliding clamp face of said sliding clamp member.

\* \* \* \* \*